(12) United States Patent
Nardeo et al.

(10) Patent No.: US 8,273,059 B2
(45) Date of Patent: Sep. 25, 2012

(54) TEARAWAY SHEATH ASSEMBLY WITH SPLIT HEMOSTASIS VALVE SEAL

(75) Inventors: Mahase Nardeo, Collegeville, PA (US); William J. McCreight, Warminster, PA (US); Nicholas P. McGrady, Lansdale, PA (US)

(73) Assignee: Medical Components, Inc., Harleysville, PA (US)

( * ) Notice: Subject to any disclaimer, the term of this patent is extended or adjusted under 35 U.S.C. 154(b) by 82 days.

(21) Appl. No.: 12/843,301

(22) Filed: Jul. 26, 2010

(65) Prior Publication Data

US 2010/0292646 A1 Nov. 18, 2010

Related U.S. Application Data

(62) Division of application No. 12/283,933, filed on Sep. 17, 2008.

(60) Provisional application No. 60/994,188, filed on Sep. 18, 2007.

(51) Int. Cl.
*A61M 5/178* (2006.01)
(52) U.S. Cl. .................. 604/164.01; 604/167.06
(58) Field of Classification Search . 604/167.01–167.06
See application file for complete search history.

(56) References Cited

U.S. PATENT DOCUMENTS

| 4,411,654 A | 10/1983 | Boarini et al. |
|---|---|---|
| 4,436,519 A | 3/1984 | O'Neill |
| 4,596,559 A | 6/1986 | Fleischhacker |
| 4,610,665 A | 9/1986 | Matsumoto |
| 4,655,752 A | 4/1987 | Honkanen et al. |
| 4,747,833 A | 5/1988 | Kousai et al. |
| 4,772,266 A | 9/1988 | Groshong |
| 4,865,593 A | 9/1989 | Ogawa et al. |
| 4,929,235 A | 5/1990 | Merry et al. |

(Continued)

FOREIGN PATENT DOCUMENTS

EP 0631793 A1 1/1995

(Continued)

OTHER PUBLICATIONS

International Preliminary Report on Patentability dated Mar. 3, 2011; PCT Application No. PCT/US08/10830.

(Continued)

*Primary Examiner* — Nicholas Lucchesi
*Assistant Examiner* — Rebecca E Eisenberg
(74) *Attorney, Agent, or Firm* — Glenn M. Massina; Fox Rothschild LLP

(57) ABSTRACT

A tearaway sheath assembly (100) having a splittable sheath tube (102) a splittable hub (110), a split valve (150,250) and a split cap (180). The valve (150,250) has a slit (158,258) at least partially across the transverse distal section (154) such that transverse distal section may be displaced laterally during insertion through the slit (158,258), of a dilator (200) or a catheter. The valve (150,250) is formed in two separate halves (152A,152B;252) that are fused or adhered to each other to form a sealed weak bond (154) that is easily broken during splitting of the sheath; each valve half is mechanically affixed in a proximal valve-receiving recess (130) of the hub such as by anchor posts (136) extending through apertures (166A, 166B) in ears (164A,164B) of each valve half. A two-part cap (180) is affixed to the hub proximal end (120) and traps the valve between itself and the hub. Pairs of opposed gaps (184, 122) of the cap (180) and the hub (110) are aligned with lines of weakness or seams (106) of the sheath tube (102) and the weak bond (154) of the valve, facilitating splitting of the assembly (100) when desired by the practitioner to peel it away from the inserted catheter.

24 Claims, 5 Drawing Sheets

U.S. PATENT DOCUMENTS

| | | | |
|---|---|---|---|
| 4,932,633 | A | 6/1990 | Johnson et al. |
| 4,983,168 | A | 1/1991 | Moorehead |
| 5,064,414 | A | 11/1991 | Revane |
| 5,085,645 | A | 2/1992 | Purdy et al. |
| 5,098,392 | A | 3/1992 | Fleischhacker et al. |
| 5,125,904 | A | 6/1992 | Lee |
| 5,154,701 | A | 10/1992 | Cheer et al. |
| 5,167,634 | A | 12/1992 | Corrigan, Jr. et al. |
| 5,207,649 | A | 5/1993 | Aruny |
| 5,221,263 | A | 6/1993 | Sinko et al. |
| 5,250,033 | A | 10/1993 | Evans et al. |
| 5,269,771 | A | 12/1993 | Thomas et al. |
| 5,304,142 | A | 4/1994 | Liebl et al. |
| 5,312,355 | A | 5/1994 | Lee |
| 5,350,363 | A | 9/1994 | Goode et al. |
| 5,397,311 | A | 3/1995 | Walker et al. |
| 5,411,483 | A | 5/1995 | Loomas et al. |
| 5,423,762 | A | 6/1995 | Hillstead |
| 5,441,504 | A | 8/1995 | Pohndorf et al. |
| 5,456,284 | A | 10/1995 | Ryan et al. |
| 5,458,640 | A | 10/1995 | Gerrone |
| 5,613,953 | A | 3/1997 | Pohndorf |
| 5,720,759 | A | 2/1998 | Green et al. |
| 5,755,693 | A | 5/1998 | Walker et al. |
| 5,885,217 | A | 3/1999 | Gisselberg et al. |
| 5,911,710 | A | 6/1999 | Barry et al. |
| 6,024,729 | A | 2/2000 | Dehdashtian et al. |
| 6,080,174 | A | 6/2000 | Dubrul et al. |
| 6,083,207 | A | 7/2000 | Heck |
| 6,197,016 | B1 | 3/2001 | Fourkas et al. |
| 6,277,100 | B1 | 8/2001 | Raulerson et al. |
| D450,839 | S | 11/2001 | Junker |
| 6,322,541 | B2 | 11/2001 | West et al. |
| 6,336,914 | B1 | 1/2002 | Gillespie, III |
| 6,387,086 | B2 | 5/2002 | Mathias et al. |
| 6,454,744 | B1 | 9/2002 | Spohn et al. |
| 6,488,674 | B2 | 12/2002 | Becker et al. |
| 6,562,049 | B1 | 5/2003 | Norlander et al. |
| 6,589,262 | B1 | 7/2003 | Honebrink et al. |
| 6,623,460 | B1 | 9/2003 | Heck |
| 6,712,789 | B1 | 3/2004 | Lange et al. |
| 6,712,791 | B2 | 3/2004 | Lui et al. |
| 6,764,464 | B2 | 7/2004 | McGuckin, Jr. et al. |
| 6,796,991 | B2 | 9/2004 | Nardeo |
| 6,808,509 | B1 | 10/2004 | Davey |
| 6,827,710 | B1 | 12/2004 | Mooney et al. |
| 6,837,873 | B1 | 1/2005 | Polley et al. |
| 6,966,896 | B2 | 11/2005 | Kurth et al. |
| 7,008,404 | B2 | 3/2006 | Nakajima |
| 7,101,353 | B2 | 9/2006 | Lui et al. |
| 7,192,433 | B2 | 3/2007 | Osypka et al. |
| 7,422,571 | B2 | 9/2008 | Schweikert et al. |
| 7,744,571 | B2 | 6/2010 | Fisher et al. |
| 2003/0085373 | A1 | 5/2003 | Dehdashtian |
| 2003/0088264 | A1 | 5/2003 | Spohn et al. |
| 2004/0059296 | A1 | 3/2004 | Godfrey |
| 2004/0102738 | A1 | 5/2004 | Dikeman et al. |
| 2004/0143219 | A1 | 7/2004 | Lee et al. |
| 2004/0193119 | A1 | 9/2004 | Canaud et al. |
| 2004/0267202 | A1 | 12/2004 | Potter |
| 2005/0010238 | A1 | 1/2005 | Potter et al. |
| 2005/0043684 | A1 | 2/2005 | Basta et al. |
| 2005/0113757 | A1 | 5/2005 | McFarlane |
| 2005/0267487 | A1 | 12/2005 | Christensen et al. |
| 2006/0030817 | A1* | 2/2006 | Kraus et al. ............... 604/167.01 |
| 2006/0145116 | A1 | 7/2006 | Rickerd et al. |
| 2006/0149293 | A1 | 7/2006 | King et al. |
| 2007/0106262 | A1 | 5/2007 | Becker et al. |
| 2007/0123825 | A1 | 5/2007 | King et al. |
| 2008/0300538 | A1* | 12/2008 | Schweikert et al. ....... 604/99.04 |
| 2009/0234290 | A1 | 9/2009 | Fisher et al. |

FOREIGN PATENT DOCUMENTS

| | | |
|---|---|---|
| EP | 1634615 A1 | 3/2006 |
| WO | 9714456 | 4/1997 |
| WO | 99/45996 | 9/1999 |
| WO | 2005013807 A2 | 2/2005 |

OTHER PUBLICATIONS

International Search Report dated Dec. 4, 2008; PCT/US2008/010830 (5 pages).

Written Opinion dated Dec. 4, 2008; PCT/US2008/0101830 (7 pages).

Office Action dated Sep. 9, 2009; U.S. Appl. No. 12/144,297 (23 pages).

Office Action dated Oct. 5, 2009; U.S. Appl. No. 12/283,933 (18 pages).

Office Action dated Mar. 23, 2010; U.S. Appl. No. 12/283,933 (7 pages).

International Preliminary Report dated Sep. 23, 2010; PCT/US2009/036486 (9 pages).

* cited by examiner

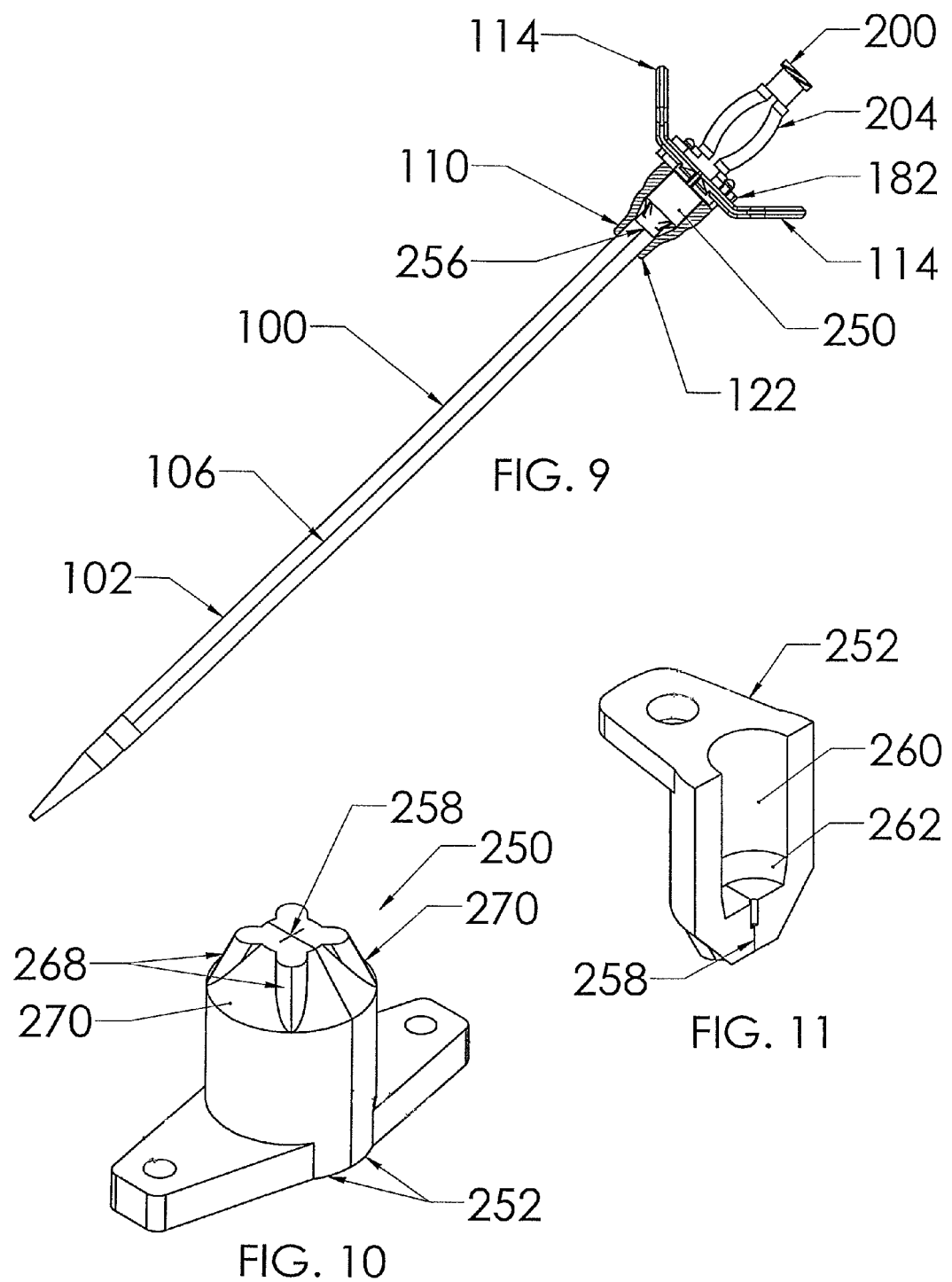

TEARAWAY SHEATH ASSEMBLY WITH SPLIT HEMOSTASIS VALVE SEAL

CROSS-REFERENCE TO RELATED APPLICATIONS

This application is a Divisional application of U.S. patent application Ser. No. 12/283,933 filed Sep. 17, 2008, which claims priority from U.S. Provisional Patent Application Ser. No. 60/994,188 filed Sep.18, 2007.

FIELD OF THE INVENTION

The invention relates to medical devices and more particularly to devices for use in insertion or implantation of catheters and the like into the vasculature of patients.

BACKGROUND OF THE INVENTION

Catheters are used in numerous medical procedures. In particular, catheters are used for the introduction or removal of fluids from various venous regions and vessels throughout the body, such as for hemodialysis. The procedure by which these catheters are introduced to the body is delicate and complex. One particularly intricate challenge to catheterization is enlarging a hole in the flesh and vessel to be catheterized while minimizing blood loss and trauma to the patient. Generally, to insert any catheter in a blood vessel, the vessel is identified by aspiration with a long hollow needle in accordance with the Seldinger technique. When blood enters a syringe attached to the needle, indicating that the vessel has been found, a thin guide wire is then introduced, typically through the syringe needle or other introducer device, into the interior of the vessel. The introducer device is then removed, leaving the guide wire within the vessel. The guide wire projects beyond the surface of the skin.

At this point, several options are available to a physician for catheter placement. The simplest option is to pass a catheter into the vessel directly over the guide wire. The guide wire is then removed. However, use of this technique is only possible in cases where the catheter is of a relatively small diameter, made of a stiff material and not significantly larger than the guide wire. If, however, the catheter is of a relatively large diameter and/or not made of a soft material, one preferable method of inserting the catheter into the vessel is through an introducer sheath. The introducer sheath is simply a large, stiff, thin-walled tube, which serves as a temporary conduit for the catheter that is being placed. The sheath is positioned by placing a dilator, which has a hollow passageway along its longitudinal axis, inside of the sheath and passing both the dilator and the sheath together into the vessel over the guide wire. The dilator expands the opening in the blood vessel to allow for catheter insertion into the vessel. The guide wire and dilator are then removed, leaving the thin-walled sheath in place. The catheter is then inserted into the vessel through the sheath.

In a setting where a catheter with a hub or other attachment at the proximal end of the catheter has a feature which is larger than that of the inner diameter of the sheath, it is necessary to have a tear-away sheath that can be split away from the catheter as the sheath is being removed from the patient. An example of such a tear-away, or splittable or peelable, sheath, with dilator is set forth in U.S. Pat. No. 6,796,991, which is depicted herein in PRIOR ART FIGS. 1 and 2 hereof. By splitting the sheath along its longitudinal axis as the sheath is being removed from the patient, the inserting physician will be able to pull out the sheath in such a way that the portion removed from the patient is split, thereby not interfering with any encumbrances on the catheter. Generally, tear-away sheaths are manufactured in a way that aids in the tearing of the sheath at two opposing points on the circumference of the sheath, thereby splitting the sheath into two halves separated longitudinally through the center of the sheath.

A sheath is generally constructed with a hub at its proximal end. This hub serves as a handle, a mating point for a dilator, and a flat surface to aid in the prevention of blood loss or contamination. When a sheath needs to be split apart in order to be successfully withdrawn from the body while leaving the catheter in place, the hub will also have to be split apart in order to clear the catheter. Preferably, the hub will split along the same lines as the sheath. To accomplish this, the hub must be designed with reveals or other weaknesses along two longitudinal lines aligned with the weaknesses in the sheath. Some previous examples of these weaknesses are tabs or webs which connect two halves of the hub, or recesses in the material comprising the hub. The weaknesses in the hub will help the inserting physician to break apart the hub in line with the tear seams on the sheath.

Another important facet of the hub is a set of tabs or wings that protrude from the center. These tabs not only help the inserting physician to align, insert and withdraw the sheath, but also to pull the sheath so that the sheath can be removed from around a catheter while still leaving the catheter in place. There are a number of different tab configurations, but it is important to have one which allows for easy maneuverability, control, and leverage. One design includes a hub wherein the tabs protrude from the hub perpendicular to a plane which includes the tear seams in the sheath and the longitudinal axis of the sheath. In this design, the tabs are diametrically opposed from each other and are spaced in such a way that when the tabs are grasped and pulled apart from each other, the sheath and its hub will split down the middle. Another desirable feature of the tabs is that the tabs provide leverage for breaking apart the hub in a manner that does not cause trauma to the incision in the body.

During insertion, especially in the time between the removal of the dilator from the sheath and the insertion of the catheter through the sheath, it is possible for blood loss through the sheath, or the introduction of contaminants or air through the sheath and into the vessel. For this reason, it is desirable that measures be taken to prevent blood, air or contaminants from traveling through the sheath. In the past, inserting physicians have simply held their thumb over the opening in the proximal end of the sheath; however, a more permanent and reliable means for preventing blood, air or contaminants from traveling through the sheath is desirable. It is therefore desirable for the hub to include a valve seal located in the sheath to traverse and seal the passageway. Such a valve seal would have at least a virtual opening therethrough that would facilitate the insertion therethrough of objects such as a catheter, dilator or syringe through the sheath while sealing thereagainst thus restricting blood loss and reducing the chance of contaminants entering the patient's bloodstream when the sheath is not engaged with a dilator or a catheter.

In the case where a sheath does not have a small diameter or a narrow point, the dilator is often used to aid in the insertion of the sheath. The dilator has a long tubular section, the outside diameter of which is slightly smaller than the inside diameter of the sheath. The dilator also has a pointed tip on its distal end and a hollow center, which runs along the entire length of the dilator. The dilator is inserted into the body with the guidewire running through its center, thereby allowing the tip of the dilator to follow the guidewire to the place that is to be catheterized. On its proximal end, the dilator may have a hub. Like the hub of the sheath, this hub can also serve a number of purposes, such as providing a stable handle to aid in guiding the dilator into the vein, and as a mechanism which can mate with the sheath hub to form a locked connection.

In PRIOR ART FIGS. 1 and 2, a releasably locking dilator and sheath assembly and methods for releasing the dilator from the sheath and longitudinally splitting the sheath are provided. The assembly includes a dilator having a dilator hub and a sheath having a sheath hub. The sheath hub has a valve and two opposing winged tabs, each tab having a perpendicular portion and an angled portion as well as a female threaded portion. The dilator hub has a male threaded portion designed to engage the female threaded portion of the sheath hub. The dilator is released from the sheath by rotating the dilator 90° in relation to the sheath and pulling the dilator out of the sheath. The sheath is longitudinally split by creating a coupling moment on each of the winged tabs thereby forcing the sheath and the sheath hub to split longitudinally. With the sheath, the valve and the sheath hub split longitudinally, the sheath is removed from around a catheter while leaving the catheter in place.

It is desired to provide a hemostasis valve for a splittable sheath, and to provide a sheath assembly with hemostasis valve and sheath hub for use therewith, that are splittable for facilitating removal of the sheath from about an inserted catheter.

BRIEF SUMMARY OF THE INVENTION

The present invention is a hemostasis tearaway sheath assembly having a splittable sheath tube and a splittable hub affixed thereto, with the hub being at the proximal end of the sheath assembly, the sheath tube extending to a smaller diameter distal sheath end, a passageway extending through the assembly from the proximal end to the distal end and defining a longitudinal axis therethrough. The sheath tube includes frangible longitudinal lines of weakness (or seams) thereal-ong to facilitate peeling or splitting during the tearaway procedure once splitting has been initiated by splitting apart of the hub by the practitioner. The assembly of the present invention also includes an easily split hemostasis valve contained and affixed within the hub.

The hub comprises two opposing sections joined to each other at frangible joints or webs until intentionally split apart, so that the hub remains an integral one-piece unit until split by the practitioner after insertion of the catheter into a patient's vasculature has been accomplished, with a grippable wing joined to each hub section for handling and for initiating splitting in a manner known in the art. The hub also provides distinct opposing gaps between the two opposing sections that are joined at frangible sections within the gaps, and upon splitting of the hub by the practitioner, the sheath tube also splits apart as the tearaway procedure continues. The easily split hemostasis valve contained within the proximal end of the hub is, prior to splitting, selectively openable to permit insertion therethrough of a dilator and later of a catheter forming a seal therewith and therearound, but otherwise remains closed to prevent blood effusion.

In a preferred embodiment, the split valve seal includes a distal slit partially across a transverse valve section, the slit being openable only to permit receipt therethrough of a dilator, syringe or catheter when same is pushed against the transverse valve section, and then closing sealingly when the device is withdrawn therethrough, and also closing sealingly about a guidewire remaining in place until catheter insertion.

Also, preferably, the valve seal comprises two opposing halves, either molded separately or, as is preferable, that are formed from an integrally molded valve seal that is bisected and then fused together to form a weak bond that is easily broken during splitting of the sheath assembly as mentioned above. Each valve seal half includes a mounting flange or ear extending laterally from its proximal end, which ear includes a post-receiving aperture. Correspondingly, the sheath hub includes a valve-receiving recess at its proximal end that includes a pair of anchor posts beside the passageway that will extend through the two post-receiving apertures of the valve seal. Further, the assembly includes a cap comprising a pair of cap halves, which remain unfixed to each other, that are fastened to the proximal hub end in a force fit so as to compress the ears of the valve seal.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 9 is an isometric view of a sheath assembly with dilator locked in position; and FIGS. 10 and 11 are, respectively, isometric views of an alternative embodiment of a complete valve and a valve half.

DETAILED DESCRIPTION OF THE INVENTION

Figure 1:
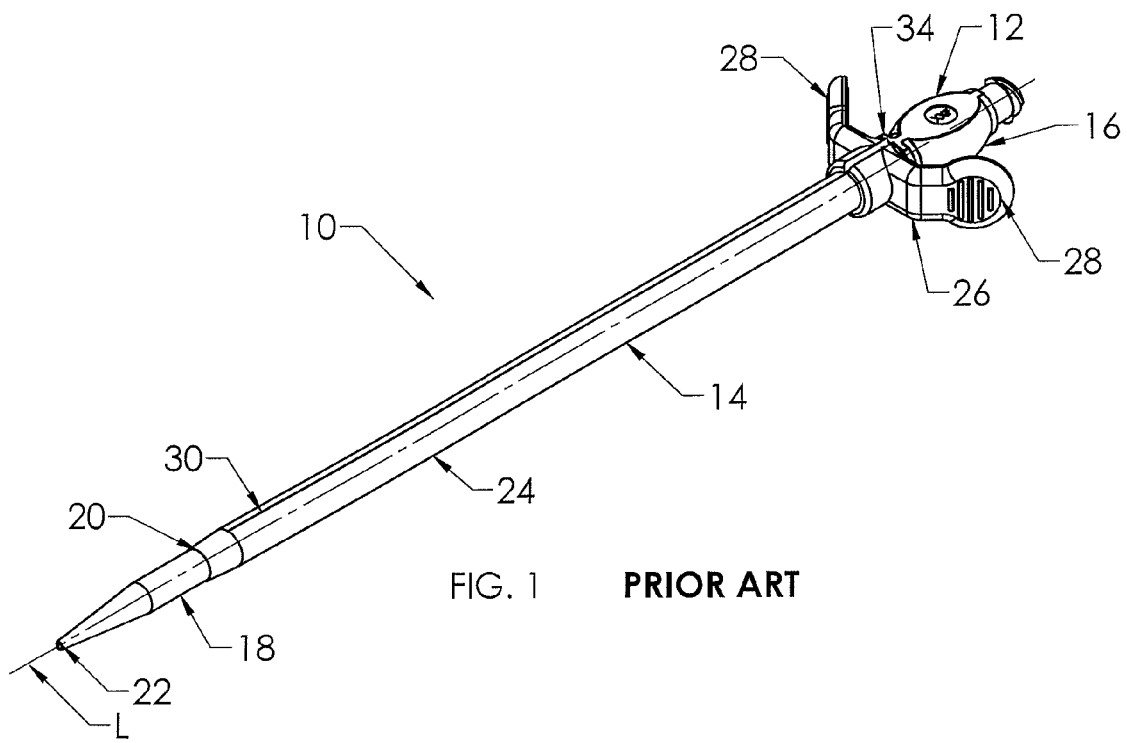
FIGS. 1 and 2 are isometric views of a PRIOR ART sheath/dilator assembly, and the sheath of the assembly shown with the dilator removed.

In the drawings, like numerals indicate like elements throughout. Certain terminology is used herein for convenience only and is not to be taken as a limitation on the present invention. The terms "distal" and "proximal" refer, respectively, to directions closer to and away from the vascular insertion site on the patient. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

Figure 2:
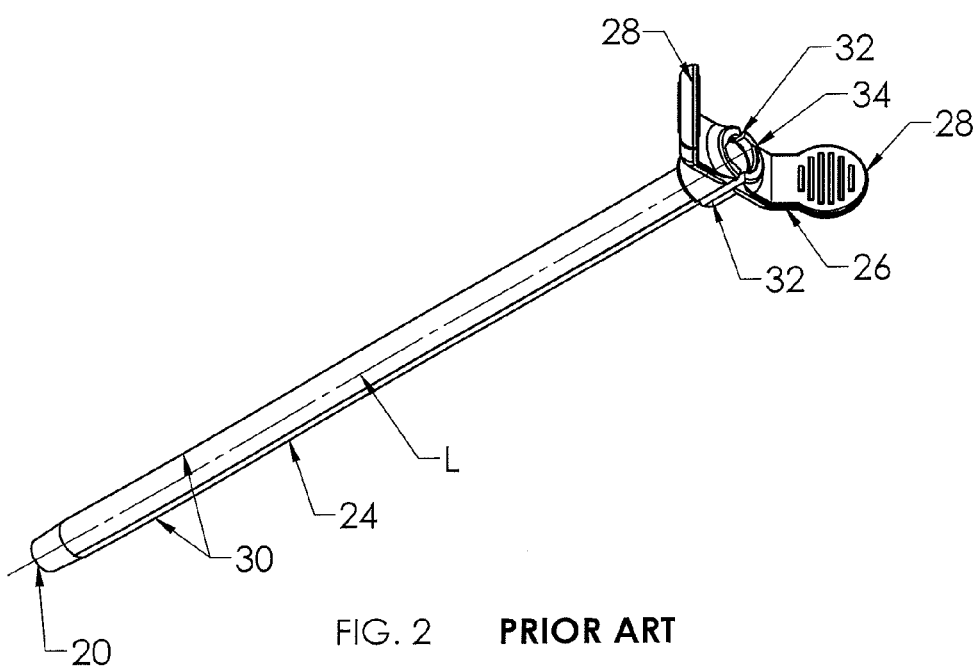

In PRIOR ART FIGS. 1 and 2, a sheath assembly 10 is shown comprising a dilator 12 and a sheath 14, and having a longitudinal axis "L". Dilator 12 has a dilator hub 16 at its proximal end, and its distal end portion 18 extends beyond the distal end 20 of sheath 14 to a distal tip 22. Sheath 14 includes a sheath tube 24 and a sheath hub 26 at the proximal end of the sheath tube, and is seen in FIG. 2 with the dilator removed. Sheath hub 26 is seen to have grippable wings 28 to facilitate the initiation of splitting by the practitioner to peel away the sheath from an inserted catheter (not shown). To facilitate splitting of the sheath 14 from around the catheter, the sheath tube has a pair of opposed frangible seams 30, and sheath hub 26 includes frangible webs along opposed gaps 32 that are aligned with seams 30. The proximal end 34 of sheath 14 includes a threaded locking arrangement for locking with the dilator hub 12 prior to removal of the dilator.

Figure 3:
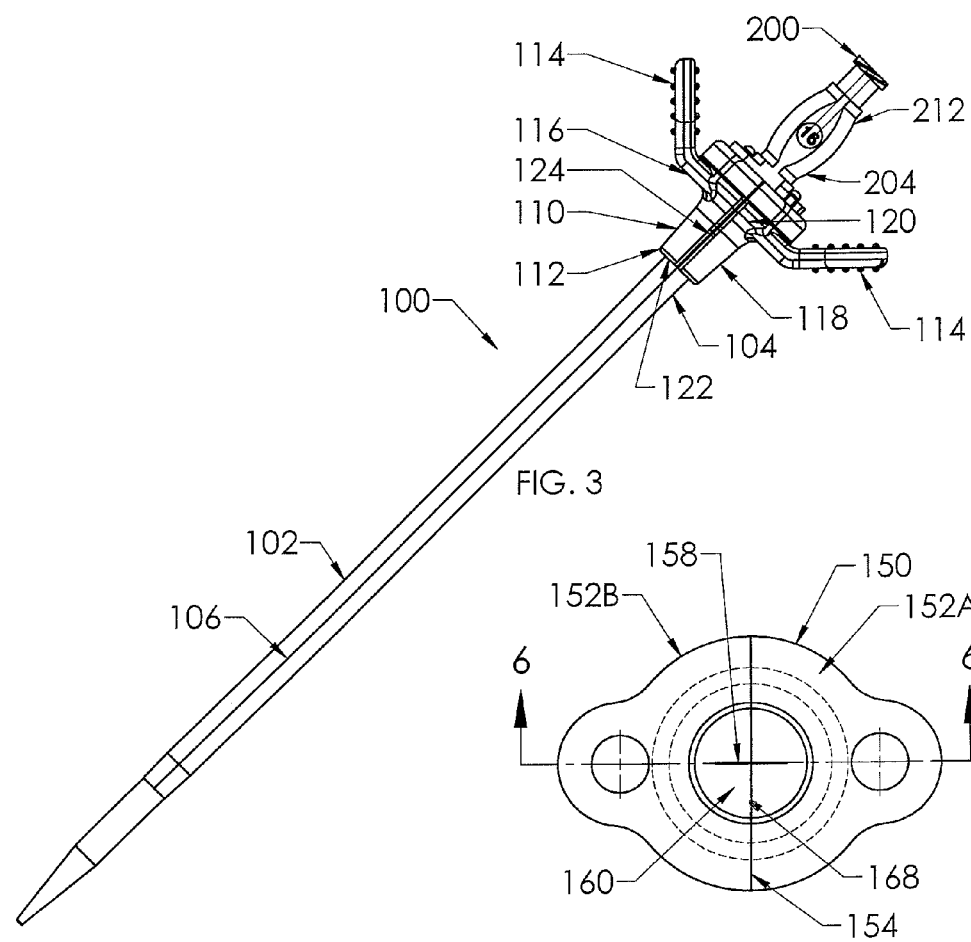
FIG. 3 is an enlarged isometric view of the tearaway sheath assembly of the present invention, showing the sheath hub and valve cap at the proximal end of the sheath tube and the hub's gaps aligned with lines of weakness of the sheath tube.
Figure 5:
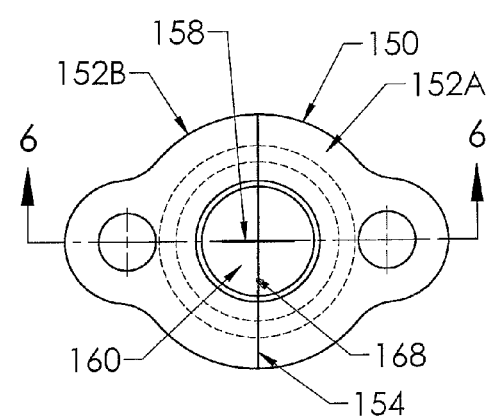
FIG. 5 is a plan view of the split valve of FIG. 4 after the two valve portions are fused together.
Figure 7:
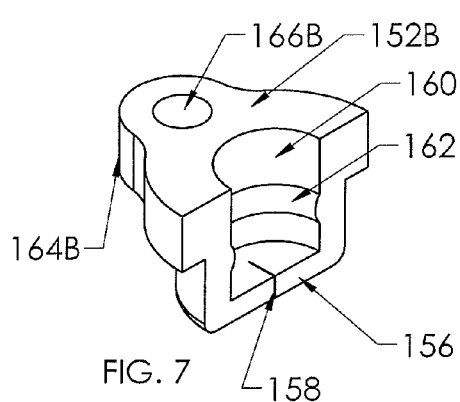
FIG. 7 is an isometric view of a half valve portion prior to valve fusion.
Figure 4:
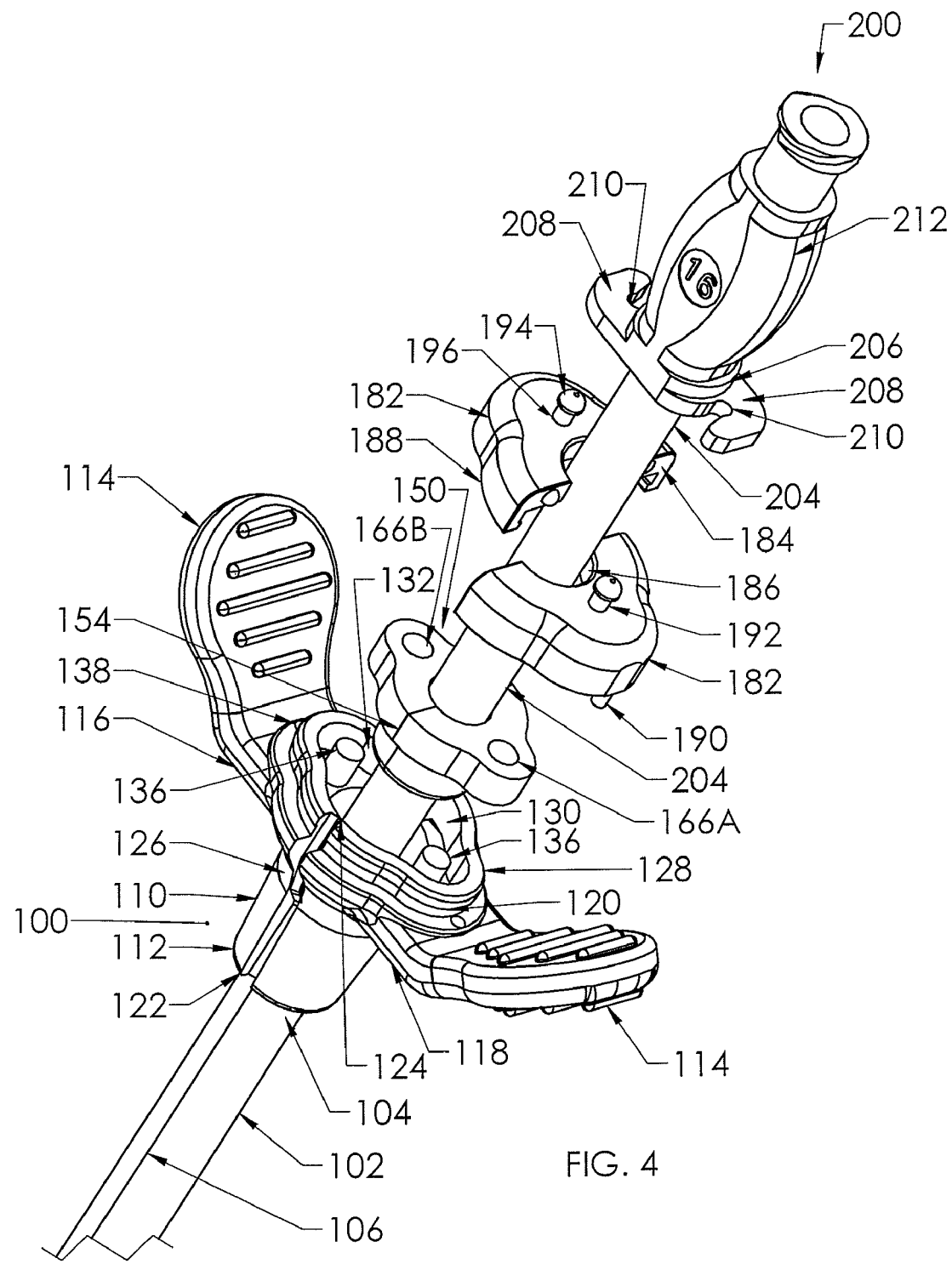
FIG. 4 is an exploded isometric view of the assembly of FIG. 3 in which are seen the valve and two separate cap halves spaced proximally from the sheath hub proximal end.

Sheath assembly 100 of the present invention is illustrated in FIGS. 3 and 4. The sheath assembly includes a sheath tube 102 with a proximal end portion 104 and extending to a distal end, with a passageway extending therebetween defining a longitudinal axis. The sheath tube 102 preferably is extruded of polytetrafluoroethylene (PTFE) having longitudinal polymeric orientation providing inherent lines of weakness represented as lines 106, for splitting therealong once splitting is initiated at the hub seams by the practitioner after completion of the insertion of the catheter's distal portion into the vasculature of a patient (not shown). Alternatively, as is shown in PRIOR ART FIGS. 1 and 2, the sheath hub can having a conventional pair of opposed seams or frangible sections 106 that define weaknesses along which the sheath tube is easily split by the practitioner.

Referring primarily first to FIG. 3, a sheath hub 110 is affixed to the proximal end portion 104 of the sheath tube, the sheath hub being affixed to the sheath tube along the distal end portion 112 of the hub. A pair of wings or tabs 114 extend from respective opposed sections 116,118 of hub 110 at its proximal end 120, for gripping by the practitioner for initiating the splitting of the sheath assembly for tearing it away from the catheter, by their being pried toward the sheath distal end such that the splitting of the hub begins at its proximal end 120 and separating hub sections 116,118 completely from each other along a pair of opposed gaps 122. A dilator 200 is disposed through the sheath with its proximal end portion 202 extending proximally from the sheath hub 110 and including a dilator hub 212. Also seen in FIG. 3 is a frangible section 124 disposed along the inside edge of gap 122 of sheath hub 110; the frangible section or webs on both sides of the hub join together the two hub sections 116,118.

Now referring to FIG. 4, hemostasis valve seal (hereinafter valve) 150 is shown exploded from hub 110, the two halves 182 of cap 180 are shown exploded from hub 110 and valve 150, and dilator hub 212 is withdrawn from the sheath enabling showing of the dilator's elongate tube 204 and clearly showing detail of the cap 180 and valve 150. Hub 110 includes a large diameter cylindrical portion 126 extending to its proximal end 120 and to a smaller diameter distal end portion 112 whereat it is affixed to a proximal end of sheath tube 102. A passageway extends through the hub 110 in fluid communication with the elongate passageway of the sheath tube 102. Proximal end 120 of hub 110 includes a proximally extending wall 128 defining therewithin a valve-receiving recess 130 having extended lateral recess portions 132 to either side of the passageway 126. Extending proximally from the recess bottom in each lateral recess portion 132 is an anchor post 136 that is generally centered with respect to the respective lateral recess portion 132 and is associated with a respective valve half. Shown just laterally outwardly of the opposite ends of wall 128 are a pair of apertures 138 for securing the cap to the hub 110, discussed later.

Hemostasis valve 150 will now be described with reference to FIGS. 4 to 7. Valve 150 includes opposing halves or portions 152A,152B that preferably are heat-fused together along a weak but sealed interfacial joint 154; alternatively, the opposing halves 152A,152B can be bonded with a weak silicone adhesive. At its distal end, valve 150 includes a transverse distal section 156. Distal section 156 includes a slit 158 therethrough extending partially to the peripheral portions thereof. Valve 150 also includes a proximal cavity 160 for receipt of the distal end of a dilator or catheter and may include an annular ridge 162 for engaging the side surfaces of the device inserted thereinto. Each valve portion 152A,152B includes a lateral flange or ear 164A,164B at its proximal end, which further includes a post-receiving aperture 166A,166B therethrough; preferably, a thick flange extends from the lateral flanges to surround the entrance to proximal cavity 160. The valve 150 may be initially molded in two separate sections or halves, or, as is preferable, initially molded as an integral whole that is bisected into opposing halves. The valve halves 152A,152B may be made of silicone and may be fused together by a weak but sealed interfacial joint 154 such as by placing the valve halves into a common conforming mold of the shape of an integral valve body and maintained at 400° F. for 1.25 hours. Optionally, an additional slit 168 can be formed through transverse distal valve section 156 partially along the weak interfacial joint 154, thus being orthogonal to slit 158.

Referring now to FIG. 4, cap 180 preferably comprises two completely separate but identical halves 182, for securing valve 150 within valve-receiving recess 130 of sheath hub 110. The interface 184 between the cap halves 182 is aligned with gaps 122 of hub 110 and seams 108 of sheath tube. Cap 180 defines a passageway 186 extending therethrough from a beveled lead-in at the cap's proximal end, with passageway 186 sufficiently large in inner diameter for a dilator and a catheter to be movably inserted therethrough. An outer cap wall 188 extends distally to be received around wall 128 surrounding valve-receiving recess 130 of hub 110, and securing posts 190 of the cap halves are snap-fitted and/or friction fitted into apertures 138 of hub 110; optionally, each cap half may also be affixed to a respective hub half-portion by adhesive. Also, optionally, the cap halves 182 may include respective protuberances and apertures along their interface 184 for precise co-alignment when assembled paired together to the hub 110.

Cap 180 may include a locking section for lockingly engaging the dilator hub 202 of the dilator 200. The locking section is shown to comprise a pair of locking pins 192 extending proximally from a proximal surfaces of the respective cap halves, each locking pin 192 including an enlarged head 194 on the end of a pin shaft 196. A distal end 206 of the dilator hub 202 includes a cooperating locking section adapted to grip the locking pins to secure the dilator in position assembled to the introducer sheath assembly 100. The cooperating locking section is shown to comprise a pair of hooks 208 that extend first radially outwardly from the side of the dilator hub distal end 204 and then circumferentially a selected small distance in a common direction, thus defining a pair of post-receiving slots 210 that are each sufficiently large to receive in a snug fit thereinto the shafts 196 of the cap's posts 192 distally of their enlarged heads when the dilator 200 is fully inserted into the sheath assembly and abutting the cap, and then rotated a small angular distance in the common direction thus moving the hooks about the locking pins.

The interrelationship of the various associated portions of the hub, valve and cap is best explained with respect to FIGS. 3 and 4. Valve 150 is seated within valve-receiving recess 130 of sheath hub 110. The anchor posts 136 of the hub 110 extending through the apertures 166A,166B of the valve ears assures that the valve halves will become separated from each other and remain with the respective hub portions when the hub is split for peeling the sheath assembly from about the catheter after catheter insertion. Similarly, the respective cap halves 182 will also remain with the respective hub portions upon splitting of the sheath hub 110.

Frangible sections or webs 124 of hub 110 that join hub sections 116,118 are formed adjacent the inside surface of the passageway of the hub and are very thin. It is preferred that, mainly for manufacturing reasons, the gaps 122 of hub 110 extend radially inwardly from hub outer surfaces to inner gap end portions that are U-shaped converging at the frangible webs 124, in order for the mold inserts to remain relatively thick, robust and durable over many molding cycles and also to carefully control the thickness of the frangible webs. The webs may have a thickness, for example, of about 0.005 in (0.127 mm), and the width of the gaps 122 at the outer surfaces can be, for example, about 0.010 in (0.254 mm).

Figure 6:
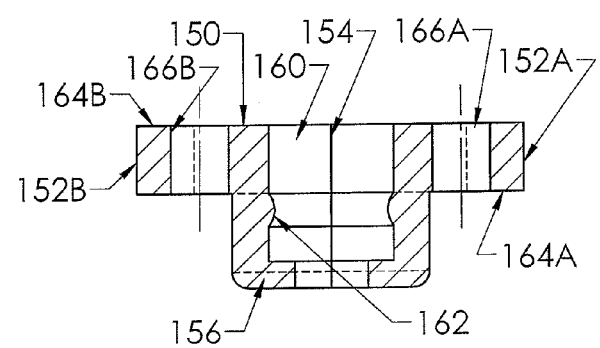
FIG. 6 is a cross-sectional view of the valve of FIG. 5 taken along lines 6-6 thereof.

It can be discerned from FIG. 6 that the transverse distal section 156 of the valve would be abutted by a proximal end of a guide wire (not shown) during initial placement of the sheath assembly over the guide wire after the guide wire is placed in the vasculature, later by the dilator distal tip inserted through the hub and valve and later by the catheter distal tip, with the slit 158 permitting an opening therethrough in response to guide wire, dilator or catheter insertion, with the valve maintaining engagement with the outer surfaces of the guide wire, dilator or catheter as it passes therethrough; and the slit will also close against the guide wire upon withdrawal of the dilator from the sheath assembly, forming a hemostasis seal and preventing effusion of blood. The hub and the cap may be made of polyethylene or polypropylene.

Figure 8:
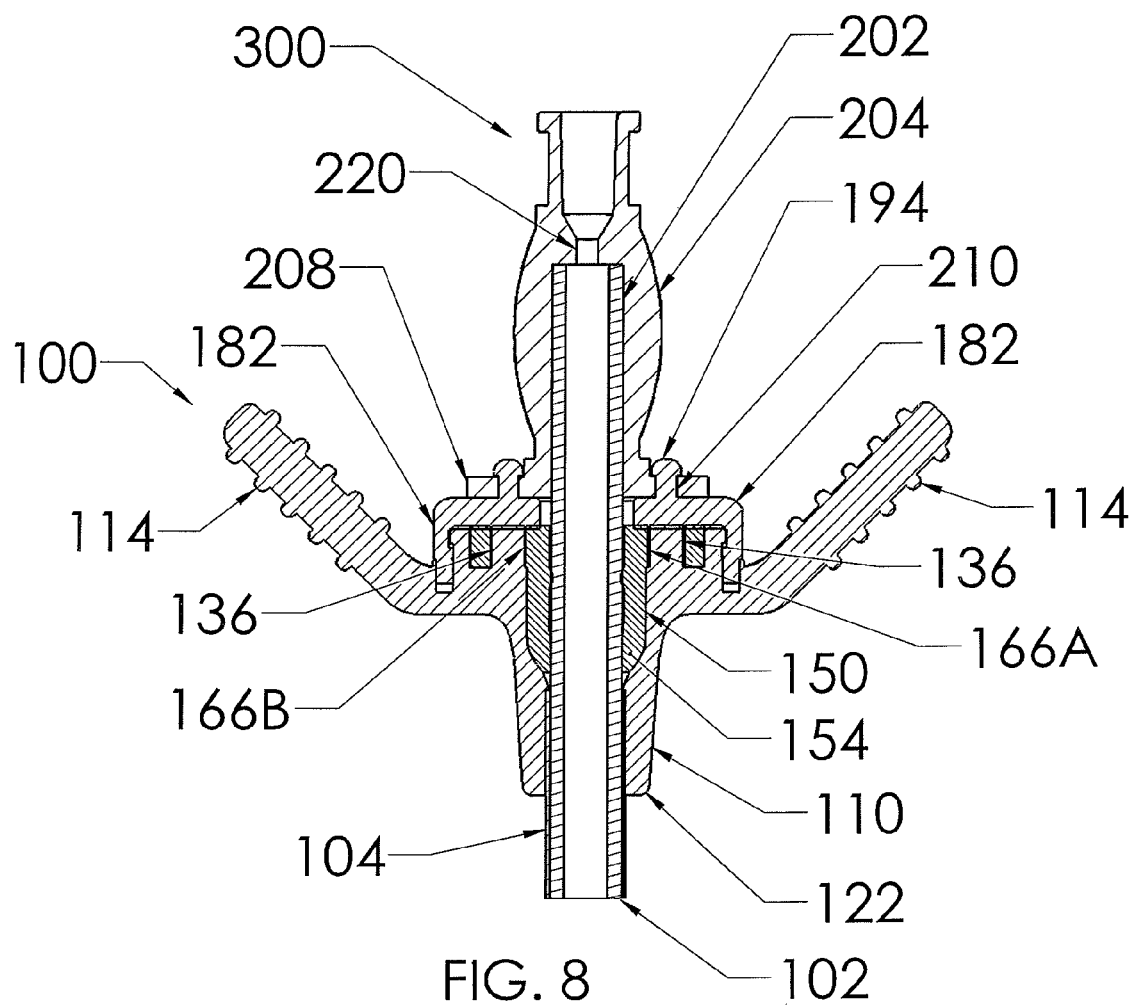
FIG. 8 is a cross-sectional view of the hub assembly with valve, with a dilator extending therethrough.

An enlarged cross-section of the proximal end of the assembly 100,200 is depicted in FIG. 8, wherein the sheath hub 110 contains the split hemostasis valve 150 seated therewithin, the cap half members 182,182 and the dilator 200 locked to the cap half members so that the dilator tube 202 extends through the valve 150 and into the sheath tube 102. The half portions of valve 150 are secured in place by posts 136 extending proximally through apertures 166A,166B. Cap posts 190 are fitted into holes in the hub half portions. Dilator hub 204 is secured to cap members 182 when hooks 208 are rotated and post-receiving slots 210 thereof are snap-fitted around locking pins 192 of the cap members. An opening 220 in the proximal portion of dilator hub 204 permits insertion therethrough of a guidewire (not shown).

A view of the entire assembly is shown in FIG. 9, partly in cross-section to show another embodiment of valve 250 in its open state, with a valve 250 and a valve half 252 illustrated in FIGS. 10 and 11, respectively. Two or more rib portions 268 are provided along outer surfaces of the converging distal end portions 270 of the valve halves 252 to enhance the closing of slit 258 either entirely, if no medical device extends therethrough, or tightly around a medical device extending therethrough, by virtue of the stiffness of the added material.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

The invention claimed is:

1. A tearaway sheath assembly for insertion of a catheter into the vasculature of a patient, comprising:
   a sheath tube, a hub and a hemostasis valve seal disposed in the hub and secured therein;
   the sheath tube having a distal end, a proximal end portion and a passageway extending therebetween, the sheath tube having longitudinal lines of weakness therealong;
   the hub having a distal end portion that is affixed to the sheath tube's proximal end portion, a proximal end and a proximal end portion, a transition portion between the distal and proximal end portions, a passageway extending therethrough, and a valve-receiving recess extending into the proximal end of the hub,
   the hub comprising two opposing sections divided by a pair of opposing gaps, the two opposing hub sections being joined together within portions of the gaps by frangible webs, with each hub section including a grippable wing extending laterally outwardly therefrom enabling initiating splitting of the sheath assembly; and
   the hemostasis valve seal having a distal end and a distal end portion, a proximal end and proximal end portion, and a passageway extending from the proximal end to a closed distal end, the valve seal adapted to seal the passageway through the assembly, and the valve seal having two initially separately formed opposed body portions having an interface therebetween and joined therealong by a sealed weak interfacial joint aligned with the gaps of the hub,
   wherein the gaps of the hub, the frangible webs of the hub and the interfacial joint of the valve seal are aligned to facilitate splitting by a practitioner upon manipulation of the wings of the hub for peeling the sheath apart and away from a catheter extending through the sheath assembly when desired.

2. The sheath assembly of claim 1, wherein the sheath tube is of polytetrafluoroethylene.

3. The sheath assembly of claim 1, wherein the sheath tube includes a pair of opposing frangible seams therealong aligned with the opposing gaps of the hub.

4. The sheath assembly of claim 1, wherein the frangible webs of the hub are provided at the transition section of the hub proximate the distal end portion and traverse the gaps.

5. The sheath assembly of claim 4, wherein the gaps at the transition section extend radially inwardly from outer surfaces of the hub to inner gap end portions that define frangible webs.

6. The sheath assembly of claim 1, further comprising a pair of anchor posts extending proximally from the proximal end of the hub within the valve-receiving recess thereof, and the valve seal includes a corresponding pair of post-receiving apertures therethrough for affixing the valve seal to the hub within the valve-receiving recess.

7. The sheath assembly of claim 1, wherein the hemostasis valve seal's sealed weak interfacial joint is formed by adhering the initially separately formed valve seal portions with silicone adhesive along the interface therebetween.

8. The sheath assembly of claim 1, wherein the hemostasis valve seal's sealed weak interfacial joint is formed by placing the initially separately formed valve seal portions, with respective faces adjacent each other along the interface, within a common conforming mold and heating same for a selected time at a selected temperature to adhere to each other along the interface.

9. The sheath assembly of claim 8, wherein the initially separately formed valve seal portions are heated together for 1.25 hours at 400° F.

10. The sheath assembly of claim 1, wherein at least one slit is defined along and through the interfacial joint across and at a center of the transverse distal section of the valve seal.

11. The sheath assembly of claim 10, wherein at least one slit is defined through the transverse distal valve section intersecting the interfacial joint at the center.

12. The sheath assembly of claim 1, wherein each hub portion includes an anchor post extending proximally into the valve-receiving recess, and the hemostasis valve seal includes a pair of opposed ears extending radially outwardly at the proximal end of each valve seal portion, each ear including defined therethrough a post-receiving aperture corresponding to a respective anchor post for anchoring the valve seal in the valve-receiving recess, whereby the valve seal is easily split in half when the tearaway sheath assembly is being removed from about a catheter being inserted into the vasculature of a patient.

13. The sheath assembly of claim 1, wherein the hemostasis valve seal includes a thick flange about its proximal end.

14. The sheath assembly of claim 1, wherein the hemostasis valve seal includes an annular interior ridge between its proximal end and the transverse distal section.

15. The sheath assembly of claim 1, further including a valve retention section securely affixed to the sheath hub proximal end after the valve seal is disposed within the valve-receiving recess.

16. The sheath assembly of claim 15, wherein the valve retention section is a cap comprising two separate halves each affixed separately to the proximal end of the hub.

17. The sheath assembly of claim 15, wherein the cap halves each include an anchor post extending distally from a distal end thereof to be force-fit into corresponding post-receiving apertures in the proximal end of the sheath hub.

18. The assembly of claim 15, wherein the valve retention section includes a pair of locking pins coextending proximally therefrom opposite each other and having enlarged heads thereon, for facilitating locking thereto of a dilator that has complementary locking sections when the dilator is inserted into the tearaway sheath assembly.

19. The assembly of claim 18, further including a dilator having a proximal hub with a pair of laterally extending hook portions at a distal end thereof, the hook portions each including a pin-receiving entrance complementary to the locking pins of the valve retention section such that the entrance openings face a common angular direction, such that the dilator is lockable to the tearaway sheath assembly when rotated in said common angular direction such that the hooks receive respective ones of the locking pins through the respective entrances.

20. The sheath assembly of claim 1, further including a valve retention section associated with the proximal end of the sheath hub, the sheath hub including a proximally extending wall defining the valve-receiving recess therewithin, and a pair of post-receiving apertures along outer sides of the wall on each hub portion, and the valve retention section being a member having an outer distally extending wall receivable along outer surfaces of the proximally extending sheath hub wall and further having a pair of anchor posts extending distally along outer surfaces of the outer distally extending wall to be received into the respective post-receiving apertures.

21. The sheath assembly of claim 20, wherein the valve retention section comprises a pair of opposing halves each including a respective anchor post, whereby each half is secured to a respective hub portion.

22. The sheath assembly of claim 1, wherein distal end portions of the valve seal portions converge and close off the passageway, a distal valve seal slit is defined transverse to the interfacial joint thereat, and each thereof includes at least one rib portion axially along an outer surface thereof offset from the line of the distal valve seal slit and having stiffness thereby resisting opening of the slit to enhance the closing of the distal end portions at the distal valve seal slit.

23. The sheath assembly of claim 1, wherein the valve seal portions are of silicone.

24. The sheath assembly of claim 1, wherein the valve seal portions are of a different material than that of the sheath assembly hub.

\* \* \* \* \*